US012692529B2

(12) United States Patent (10) Patent No.: US 12,692,529 B2
Donia et al. (45) Date of Patent: Jul. 28, 2026

(54) QUANTITATIVE SCREEN FOR THE ASSESSMENT OF INTER-INDIVIDUAL VARIABILITY IN DRUG METABOLISM BY THE HUMAN GUT MICROBIOME

(71) Applicant: The Trustees of Princeton University, Princeton, NJ (US)

(72) Inventors: Mohamed Abou Donia, Princeton, NJ (US); Bahar Javdan, Fort Lee, NJ (US); Jaime Lopez, Surprise, AZ (US)

(73) Assignee: The Trustees of Princeton University, Princeton, NJ (US)

( * ) Notice: Subject to any disclaimer, the term of this patent is extended or adjusted under 35 U.S.C. 154(b) by 719 days.

(21) Appl. No.: 17/928,688

(22) PCT Filed: Jun. 1, 2021

(86) PCT No.: PCT/US2021/035186
§ 371 (c)(1),
(2) Date: Nov. 30, 2022

(87) PCT Pub. No.: WO2021/247527
PCT Pub. Date: Dec. 9, 2021

(65) Prior Publication Data
US 2023/0212640 A1 Jul. 6, 2023

Related U.S. Application Data

(60) Provisional application No. 63/033,306, filed on Jun. 2, 2020.

(51) Int. Cl.
*C12Q 1/02* (2006.01)
*G16B 20/00* (2019.01)
(52) U.S. Cl.
CPC ............. *C12Q 1/025* (2013.01); *G16B 20/00* (2019.02); *C12Q 2600/106* (2013.01)
(58) Field of Classification Search
CPC .. C12Q 1/025; C12Q 2600/106; G16B 20/00; G16B 40/20; G01N 2570/00
See application file for complete search history.

(56) References Cited

U.S. PATENT DOCUMENTS 5,279,964 A * 1/1994 Chrisope ................ C12M 47/00
435/309.3
9,878,984 B2 1/2018 Huang et al.

2012/0208282 A1 8/2012 Deigner et al.
2014/0045744 A1* 2/2014 Gordon .................... C12Q 1/04
435/252.4
2016/0263166 A1* 9/2016 Elinav .................. A61K 35/741
2020/0138821 A1 5/2020 Hackam et al.

FOREIGN PATENT DOCUMENTS

WO 2019178542 A1 9/2019
WO 2020009916 A1 1/2020
WO 2020252257 A1 12/2020

OTHER PUBLICATIONS

Matysik, S et al. Metabolomics of fecal samples: a practical consideration. Trends in Food Science & Technology. 2016. 57: 244-255. (Year: 2016).*
Roberts, LD et al. Targeted metabolomics. Current Protocols in Molecular Biology. 2012. Chapter 30: 30.2.1-30.2.24. (Year: 2012).*
Gregory, KE et al. Method development for fecal lipidomics profiling. Analytical Chemistry. 2013. 85: 1114-1123. (Year: 2013).*
Harrison, DA et al. Sample size and power calculations using the noncentral t-distribution. The Stata Journal: Promoting Communications on Statistics and Stata. 2004. 4(2): 142-153. (Year: 2004).*
International Search Report and Written Opinion for corresponding PCT Application No. PCT/US2021/035186, dated Oct. 28, 2021.
Liou et al., "A Metabolic Pathway for Activation of Dietary Glucosinolates by a Human Gut Symbiont", Cell, vol. 180, Iss. No. 4, pp. 717-728, Feb. 20, 2020.
Javdan et a.l "Personalized Mapping of Drug Metabolism by the Human Gut Microbiome," Cell, Jun. 10, 2020 (Jun. 10, 2020), vol. 181.1ss.7,pp. 1661-1679.

* cited by examiner

*Primary Examiner* — David W Berke-Schlessel
*Assistant Examiner* — Susan E. Fernandez
(74) *Attorney, Agent, or Firm* — Meagher, Emanuel , Laks, Goldberg & Liao, LLP

(57) ABSTRACT

Disclosed herein is a quantitative screen for the assessment of microbiome derived drug metabolism. The disclosed quantitative screen, named MDMQ-Screen, may be employed, inter alia, for assessing the impact of the human gut microbiome on drug metabolism. MDMQ-Screen is used to measure and explain inter-individual variability in drug metabolism. This information is crucial in explaining potential toxic effects of the administered drugs, as well variability in response to therapy between individuals. Inter alia, MDMQ-Screen can be used to assess unexplained variability in drug response and toxicity of already used medications; used in future drug development pipelines to aid in the design and interpretation of clinical trials; and used at bedside to assess the probability of drug response and toxicity and provide recommendations for therapeutic modifications in a personalized medicine manner.

14 Claims, 12 Drawing Sheets

*200*

*210*     *Receive Patient Diagnosis/Suggested Treatment and MDM-QScreen Results*

*215*     *Calculate Values of Treatment Options and Adjustments*

*220*     *Determine Sufficiency of Suggested Treatment*

*225*     *Send Adjusted Treatment/Dosage*

*300*

*310* — Receive Compound Structures and MDM-QScreen Results

*315* — Identify Distinct Structural Components of Compounds

*320* — Correlate Identified Components with MDM-Qscreen Results

*325* — Receive New Compound Structure

*330* — Provide Suggestions For Improving Compound Structure

1

QUANTITATIVE SCREEN FOR THE ASSESSMENT OF INTER-INDIVIDUAL VARIABILITY IN DRUG METABOLISM BY THE HUMAN GUT MICROBIOME

CROSS-REFERENCE TO RELATED APPLICATIONS

This application claims priority to U.S. Provisional Pat. App. No. 63/033,306, filed Jun. 2, 2020, and is incorporated herein by reference in its entirety.

STATEMENT REGARDING FEDERALLY SPONSORED RESEARCH OR DEVELOPMENT

This invention was made with government support under Grant No. AI124441 awarded by the National Institutes of Health. The government has certain rights in the invention.

BACKGROUND

The human gut microbiome is composed of hundreds of individual species of bacteria and varies greatly between individuals. It has been shown for more than 70 years that bacterial isolates from the gut microbiome can directly metabolize clinically used drugs, with important clinical implications (e.g., effects on toxicity or therapeutic efficacy). Despite this knowledge, the exact contribution of the gut microbiome to drug pharmacokinetics has not been considered in the drug development pipeline.

BRIEF SUMMARY

The approach disclosed herein provides a quantitative screen that directly measures the ability of the collective human gut microbiome to metabolize any active material (such as a drug) of interest: microbiome-derived metabolism quantitative screen (MDMQ-Screen). This screen does not rely on single isolates of the gut microbiome, but instead takes into account the collective contribution of complex microbial communities that are derived from the gut microbiome. Importantly, MDMQ-Screen accomplishes this goal in a subject-personalized manner, and quantifies the inter-individual variability between subjects with respect to their MDM. By discovering new drug-microbiome interactions, and quantifying their inter-individual variability, MDMQ-Screen can be used to explain non-linear pharmacokinetic and toxicity profiles for currently used drugs, inform future drug design and formulation for newly developed drugs, and guide efforts for personalized medicine.

The disclosed approach for quantitatively assessing drug metabolism generally comprises at least five steps: (i) providing one or more fecal samples from one or more donors; (ii) producing an ex vivo culture of a donor microbiome (such as human gut microbiome) from the fecal samples in a predetermined medium; (iii) incubating the ex vivo culture of the donor microbiome with at least one active material (such as a pharmaceutical composition intended to be taken orally, or non-orally); (iv) chemically extracting a sample from the ex vivo culture and a control; and (v) analyzing the extracted samples and quantifying drug and metabolite levels in at least one of the extracted samples using a quantitative targeted metabolomics assessment. The approach preferably also includes identifying a novel metabolite in the extracted sample using a quantitative untargeted metabolomics assessment.

2

The method also includes preserving at least a portion of one or more fecal samples. This may optionally be done by, e.g., bringing each fecal sample into an anaerobic environment, suspending a portion of each fecal sample in a sterile buffer with an amino acid, allowing a supernatant to form, and mixing the supernatant with a preservative at a predetermined ratio. Optionally, the sterile buffer is sterile phosphate buffer supplemented with L-cysteine, where the L-cysteine is present in the sterile phosphate buffer in an amount less than 0.5 wt %. Optionally, the mixture may be frozen after the preservative has been added.

In some embodiments, such as when the control sample and the sample from the ex vivo culture both comprise a metabolite, the quantification step (step v) includes determining whether the sample from the ex vivo culture contains a different metabolite, such as a derivative of the active material, as compared to the control sample.

In some embodiments, the quantification step (step v) includes determining whether the at least one active material can be detected in the control sample and not detected in the sample from the ex vivo culture.

In some embodiments, the active material is present in the incubated ex vivo culture at a concentration ≤50 µM.

If the active material is within a pharmaceutical composition, in some embodiments the pharmaceutical composition is one that is intended to be taken orally. In some embodiments, the pharmaceutical composition is one that is not intended to be taken orally, including but not limited to compositions intended to be administered topically, intraperitoneally, intravenously, intraarterially, transdermally, subcutaneously, intramuscularly, intranasally, via inhalation, or intraocularly, In some embodiments, the predetermined medium is selected utilizing a metric: Expected Number of Detectable Strains (ENDS), where the contribution of each amplicon sequence variant (ASV) is weighed by the probability that its metabolite can be detected while considering total biomass. Preferably, this includes selecting the medium having the highest value for ENDS.

In some embodiments, the extracted samples are analyzed using High Performance Liquid Chromatography coupled with High-Resolution Mass Spectrometry (HPLC-HRMS).

DETAILED DESCRIPTION

Figure 1:
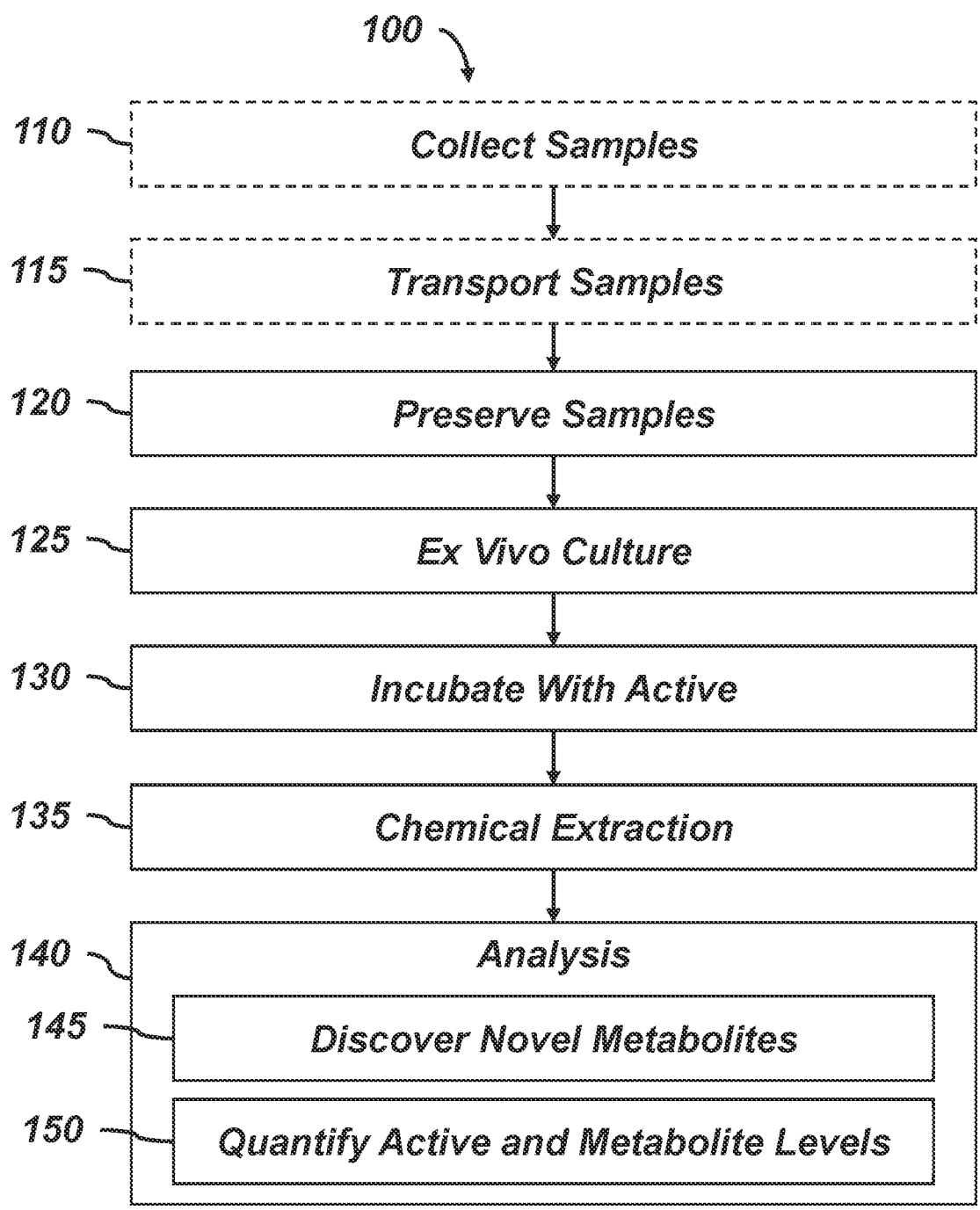
FIG. 1 is flowchart of an embodiment of a disclosed method.

MDMQ-Screen can be used to discover, measure and explain inter-individual variability in drug metabolism that is attributed to the gut microbiome. This information is crucial in explaining potential toxic effects of administered drugs, as well as variability in response to therapy between individuals. It is also important in understanding the mechanistic basis for how drugs are metabolized in the body, and to inform changes in drug design.

It is expected that this platform can be used in at least four different applications: (1) it can be used to assess unexplained variability in drug response and toxicity of already used medications; (2) it can be used in future drug development pipelines to aid in the design and interpretation of clinical trials; (3) it can be used to inform drug design, where an undesired effect of the microbiome on the drug under development can be discovered and eliminated early on in the process; and (4) it can be used to assess the probability of drug response and toxicity, and provide clinical recommendations for therapeutic modifications in a personalized medicine manner.

In drug development, in both pre-clinical and clinical phases, the contribution of the gut microbiome is almost completely overlooked. The general ADME (Absorption, Distribution, Metabolism, Excretion) and pharmacokinetics studies look at the overall fate of the studied drug in animal models or humans, but do not differentiate whether these effects are contributed by the human body (e.g., liver, intestine, kidneys) or by the human gut microbiome. This lack of knowledge leads to an incomplete picture about the ADME and pharmacokinetics of the studied drugs in cases where the contribution of the gut microbiome is important. Three problems could arise as a result of this:

First, in cases where the human gut microbiome significantly degrades an administered oral drug prior to its absorbance, the bioavailability of this drug may be diminished. To correct for this effect during drug development, the dose of the drug may be increased to achieve adequate therapeutic response, but this increase may lead to other side effects in addition to the economic cost. MDMQ-Screen provides a solution to this first problem in that it can provide a quantitative measure of the ability of the complex gut microbiome to degrade orally administered medications over time. With this knowledge in hand, alternative formulations can be used, or other microbiome-targeted strategies can be employed. As of now, there is no standardized assay to accomplish this goal.

Second, in cases where the gut microbiome of one individual metabolizes a given oral drug in a different manner than the gut microbiome from another individual, inter-individual variability in the ADME of the administered drug may be observed. Examples of this include cases where the drug is degraded by one individual's microbiome but not by another, or ones where the drug is converted into a toxic metabolite by one individual's microbiome and not by another. During drug development, this variability could lead into convoluted clinical results and even failed clinical trials. MDMQ-Screen provides a solution to this second problem in that it can provide a quantitative measure of inter-individual variability in drug metabolism, both with regards to drug degradation and to the conversion into new metabolites (including toxic ones). This information can be considered during the clinical trial analysis, allowing scientists to quantitatively factor in the microbiome contribution to the observed variation in ADME, response, or toxicity between different subjects in the clinical trial. As of now, there is no standardized assay to accomplish this goal.

Third, inter-individual variability in drug response and toxicity is common with established drugs, but the contribution of the human gut microbiome to it is rarely studied. Despite this variability, whether it is contributed by the human gut microbiome or other factors, different patients are often prescribed the same medications. There is a dire need to know beforehand whether a drug may be affected by the patient's microbiome (possibly leading to undesired responses). MDMQ-Screen provides a solution to this third problem in that it can provide a personalized measure of drug metabolism by the gut microbiome, which can be performed prior or during therapy to determine potential adverse effects or sub-adequate responses mediated by the gut microbiome.

One embodiment of a general process of executing MDMQ-Screen can be seen with reference to FIG. 1. In FIG. 1, the method (100) begins by optionally collecting (110) at least one fecal sample from at least one donor (e.g., in a sterile container, etc., as appropriate). In some embodiments, samples are collected from a plurality of donors. In some embodiments, samples are collected from at least 10 donors. In some embodiments, samples are collected from at least 20 donors.

In some embodiments, other information about each donor is also collected, such as age, health status (including diseases, infections, antibiotic usage, etc.). Each donor is preferably assigned a donor ID as well.

In some embodiments, each donor is human. In some embodiments, each donor is a mammal. In some embodiments, each donor is a non-human animal. In some embodiments, each donor is within a predefined age range, sex, and/or ethnic group.

If fecal samples are collected, the method may also optionally include transporting (115) the samples, e.g., to a storage location or a laboratory. In some embodiments, each sample is transported "on ice" or otherwise kept at a lowered temperature (such as <20° C., ≤15° C., ≤10° C., ≤5° C.). This may be done in any appropriate manner, including, e.g., keeping the sample(s) in a sealable container with ice or dry ice. In embodiments, samples transported for a predetermined period of time or longer are kept on ice, while samples transported for less than the predetermined period of time are not kept on ice. For example, in one embodiment, samples transported for less than 15 minutes were not kept on ice, while samples transported for 15 minutes or longer required transportation on ice. In some embodiments, a maximum transportation time is enforced, such as limiting the transportation time to 30 minutes or 60 minutes.

After fecal samples are collected, the method includes preserving (120) the collected samples. In some embodiments, the method includes preserving at least a portion of one or more fecal samples. This can be done in a variety of ways, including, e.g., by bringing each fecal sample into an anaerobic environment, suspending a portion of each fecal sample in a sterile buffer with an amino acid, allowing a supernatant to form, and mixing the supernatant with a preservative at a predetermined ratio. The mixture may then be frozen after the preservative has been added. In some embodiments, the sterile buffer is sterile phosphate buffer supplemented with L-cysteine, where the L-cysteine is present in the sterile phosphate buffer in an amount less than 0.5 wt %.

In a preferred embodiment: (i) samples are brought into an anaerobic chamber (e.g., 70% $N_2$, 25% $CO_2$, 5% $H_2$); (ii) one gram of each sample is suspended in a sterile buffer supplemented with an amino acid or derivative of an amino acid (e.g., 15 ml of sterile phosphate buffer supplemented with 0.1% L-cysteine (PBSc) in a 50 ml sterile falcon tube); (iii) allowing suspension to sit for a period of time (e.g., leaving the suspension standing still for 5 min to let insoluble particles settle) to obtain supernatant; (iv) suspending the supernatant with a glycerol solution (e.g., an equal volume of 40% glycerol in PBSc); and (v) sample aliquots (1 ml) of this suspension are placed in sterile cryogenic vials and frozen (preferably at −80° C.) until use. Samples may be assigned de-identifying numbers and stored as, e.g., donor glycerol stocks.

When additional work is ready to begin, the samples to be tested are provided. An ex vivo culture of a donor's microbiome may be produced (125) in at least one medium. The donor microbiome may be any appropriate microbiome, including, e.g., a human gut microbiome.

In one embodiment, each donor's glycerol stock was provided, and 30 µl of each was used to separately inoculate 3 ml of 10 different pre-reduced media in replicates: Liver Broth (Liver), Bryant and Burkey Medium (BB), Thioglycolate Broth (TB), Luria-Bertani Broth (LB) (obtained from Sigma Aldrich, USA), Brain Heart Infusion (BHI), MRS (MRS), Reinforced Clostridium Medium (RCM), modified Gifu Anaerobic Medium (mGAM) (obtained from HyServe, Germany), Gut Microbiota Medium (GMM (Goodman et al., 2011)), and a 70:30 mix of BB:GAM (BG).

Preferably, an optimal medium is selected. More preferably, an optimal, predetermined medium is selected utilizing a metric called Expected Number of Detectable Strains ("ENDS"), where the contribution of each amplicon sequence variant (ASV) is weighed by the probability that its metabolite can be detected while considering total biomass.

Expected Number of Detectable Strains (ENDS)

ENDS estimates the number of strains for which microbiome-derived metabolism (MDM) reactions can be experimentally detected in ex vivo cultures. ENDS answers the following question: if all of the Amplicon sequencing variants (ASVs) in the ex vivo culture performed an MDM reaction at a given rate (in units of normalized metabolite signal per unit biomass per time), how many ASVs' reactions will be detected in the screen given the culture composition and measurement instrument? Preferably, this includes selecting the medium having the highest value for ENDS.

The ENDS framework is needed to incorporate the potentially confounding impact of community biomass in the media selection process. For example, if biomass is not considered, a high-diversity low-density community where bacterial load is too low to produce detectable metabolite levels would be favored over a lower diversity community with high enough bacterial load to produce detectable metabolite levels. Formally one is computing the expected value of the number of reactions detected:

$$E[N_s] = \sum_{i=1}^{n} B(x_i)$$

Where $E[N_s]$ is the expected number of detectable microbes, and $B(x_i)$ is the probability of microbe i's reaction being detected with an absolute population of size $x_i$. How can one construct $B(x_i)$? In statistical terms, $B(x_i)$ is equivalent to the power (the probability of deciding there is a reaction when the reaction is actually present) of the hypothesis testing method used to analyze the data. In these examples, a one-sided unequal variation t-test with cutoff $\alpha$ was used. Now that one has a framework for calculating $B(x_i)$, one must relate a given $x_i$ to a null and alternative distribution of measurements.

One assumes that the metabolite measurements are composed of two types of signal: background noise, X, and compound signal, Y. Both signals are assumed to be normally distributed. The background noise $X \sim N(\mu_1, \sigma_1)$ is the signal present when no actual metabolite is present. The compound signal $Y \sim N(\mu_2, f(\mu_2))$ is the portion of the signal due to measurement of an actual metabolite. The measurements in the control condition are modeled by X while the measurements in the experimental condition are modeled as $$Z = X + Y \sim N\left(\mu_1 + \mu_2, \sqrt{\sigma_1^2 + f(\mu_2)^2}\right).$$

One can now relate the population abundance $x_i$ to the mean of Y, $\mu_1$. In real terms, $\mu_1$ is the average level of a metabolite produced by $x_i$. One can assume the production metabolite is governed by the dynamics $$\frac{d[M]}{dt} = r x_i,$$

where [M] is the concentration of the metabolite and r is the rate of metabolite production per cell. If one assumes the drug is added at stationary phase such that $$\frac{dx_i}{dt} = 0$$

for all t after drug addition, the total amount of metabolite produced is $[M]=\tau r x_i$, where $\tau$ is the incubation time. The r can vary widely, and to account for this, it can be set using the rate of a known MDM reaction.

One must now estimate the distribution of X. One can estimate this by computing the mean and standard deviation of spurious peaks detected when samples not containing the compound being measured is quantified. Now one must define the standard deviation of Y, f ($\mu_2$). This is clearly dependent on the instrument being used. By plotting the standard deviation of triplicate measurements from a given machine against their mean, one can estimate f ($\mu_2$). To ensure one is capturing only measurement signal, one can base the model only on measurements that are largely composed of measurement signal (more than three standard deviations above the mean of the null distribution). It has been found that a power law $$f(\mu_2) = \alpha \mu_2^b$$

fits the data well. With the distribution of X and Z, one can then estimate the B($x_i$) using existing methods (Harrison and Brady, 2004. Sample Size and Power Calculations using the Noncentral t-distribution. The Stata Journal 4, 142-153).

What if one wants to create an ensemble of multiple culture conditions to detect even more microbial reactions? To do this, one can define the expected number of new detectable microbes gained if one includes another media E[$\Delta N_s$]. For each ASV in all media, one can take the product of the probability that the reaction is not detected in the existing media and the probability that the reaction is detected in the new media $$E[\Delta N_s] = \sum_{i=1}^{n} B(x_i) \prod_{j=1}^{m} \left(1 - B\left(y_i^j\right)\right)$$

where m is the number of media in the existing ensemble and $$y_i^j$$

is the abundance of ASV i in existing media j. In example computations of ENDS, samples with less than 10,000 reads were excluded, and the optimal media was taken as the one with the highest ENDS averaged across twenty donors.

Referring again to FIG. 1, after the ex vivo cultures are prepared in whatever medium or media are deemed appropriate, the culture is incubated (130) with an active material (such as a drug of interest, etc.), along with appropriate controls. In some embodiments, the active comprises an active pharmaceutically ingredient (API). In some embodiments, the active material is within a pharmaceutical composition, which may be, e.g., a composition intended for oral consumption. In some embodiments, the active comprises a biological material such as a protein or peptide. In some embodiments, the active material is a chemical compound, e.g., from a small molecular library. In some embodiments, all active materials are: (i) selected from a particular class of pharmaceutical compositions; and/or (ii) selected from a group of pharmaceutical compositions believe capable of treating a specific condition. For example, it may be useful to screen a particular patient for an optimal anti-anxiety medication by screening (i) all benzodiazepines (i.e., a particular class of drug) or all drugs known to increase the action of gamma-aminobutyric acid (i.e., a slightly broader class of drug), or (ii) all of the anti-anxiety medications in the market (i.e., a group capable of treating a specific condition).

In some embodiments, the ex vivo cultures are allowed to incubate for a period of time before an active material is added. In other embodiments, the active material is added prior to the any incubation.

In some embodiments, the concentration of the active material in the incubating ex vivo culture is $\leq 1$ M, $\leq 100$ mM, $\leq 1$ mM, $\leq 100$ µM, $\leq 50$ µM, $\leq 25$ µM, $\leq 10$ µM, $\leq 5$ µM, or $\leq 1$ µM.

For example, in some embodiments, in an anaerobic chamber, a small volume (~100 µl) of each donor glycerol stock was diluted in 1 ml of mGAM, and then 20 µl of this solution was used to inoculate 3 ml of mGAM in culture tubes. Cultures were grown for 24 hours at 37° C. in an anaerobic chamber. After 24 hours, 10 µl of one or more active materials from a particular screening library were added (the concentration of each molecule in the library being 10 mM in DMSO), or of a DMSO control were added to the growing microbial community. In addition, 10 µl of each active material was also incubated similarly in a no-microbiome, mGAM control. The experimental and control samples were then allowed to incubate under the same conditions for a second 24-hour period.

In another example, a new medium, BG, was made as follows: BB powder and mGAM powder were reconstituted in water and autoclaved as per manufacturer instructions (Sigma and Hyserv, respectively). Liquid BB medium was mixed with liquid mGAM in a 70:30 ratio, respectively. For each donor, 500 µl of a donor's glycerol stock was used to inoculate 50 ml of pre-reduced BG medium and incubated for 24 hours in an anaerobic chamber at 37° C. The culture was transferred to a sterile Nunc 96-well plate (Fisher Scientific) with each well containing 400 µl of culture. 13.2 µl of each active material stock solution (1 mM in DMSO), or 13.2 µl of DMSO as a vehicle-only control, were pipetted and resuspended in 4 adjacent wells of the 96-well plate (quadruplicates). The plate was then incubated for 24 hours anaerobically at 37° C.

After incubation, samples can be chemically extracted (135) from the experimental and control cultures.

This can be accomplished using appropriate known chemical extraction techniques, such as solvent extraction using appropriate solvents. In some embodiments, organic solvents are used. In some embodiments, the organic solvent is a C1-C4 alkyl acetate (e.g., methyl acetate, ethyl acetate, butyl acetate, etc.) a C1-C4 methyl ketone (e.g., methyl isobutyl ketone, methyl ethyl ketone (MEK)), methanol, or acetonitrile.

In one example, after incubation, cultures were extracted with double volume of ethyl acetate and the organic phase was dried under vacuum using a rotary evaporator (Speed Vac). The dried extracts were suspended in 250 µl MeOH, centrifuged at 15,000 rpm for 5 min to remove any particulates.

In another example, with samples in a 96-well plate, 10 µl of an internal standard (voriconazole, 1 mM) was pipetted into the wells, for use with targeted metabolomics techniques. Then, 800 µl of ethyl acetate was pipetted into the wells and resuspended three times. 400 µl was pipetted into an Agilent 96-well plate and dried under Nitrogen with a 96-well blow-down evaporator (Fisher Analytical).

After chemical extraction, the extracted samples can be analyzed (140). Preferably, this analysis comprises the use of High Performance Liquid Chromatography coupled with High-Resolution Mass Spectrometry (HPLC-HRMS). During this analysis, active and metabolite levels can be quantified (150) using a quantitative targeted metabolomics approach/technique in MDMQ-Screen, and novel microbiome-derived metabolites of the active material can be identified (145) using a quantitative untargeted metabolomics approach/technique. These two steps (targeted and untargeted metabolomics approaches) can be performed in any order or done in parallel.

In some embodiments, where the control sample and the sample from the ex vivo culture both comprise a metabolite, the quantification of active material and metabolite levels may comprise determining whether the sample from the ex vivo culture contains a different metabolite as compared to the control sample, such as a derivative of the active material.

In some embodiments, the quantification of active material and metabolite levels may comprise determining whether the at active material can be detected in the control sample and not detected in the sample from the ex vivo culture.

Example Analysis Using a Targeted Metabolomic Approach

In an example, a 96-well plate was resuspended in 300 µl methanol and left for 10 min at room temperature prior to centrifugation at 3900 RPM for 10 min at 4° C. 60 µl were carefully decanted from the top into a new plate with 60 µl methanol and run on an Agilent 6545 LC/QTOF machine (0.5 µl injection, only three of the four replicates for each drug were run on the machine). The remaining 240 µl were dried and stored at −20° C. for future runs. An abiotic BG-drug plate and a heat-killed-microbiome-drug plate were prepared and analyzed using the same method, serving as controls to estimate non-enzymatic drug degradation or metabolite production. To prepare the heat-killed-microbiome plate, 500 µl of D20 glycerol stock was used to inoculate 50 ml of pre-reduced BG media and incubated for 24 hours in an anaerobic chamber at 37° C. The culture was heat-killed at 100° C. for 30 minutes while keeping the flask containing it sealed (and therefore maintaining the anaerobic conditions). Drug incubation, chemical extraction, and HPLC-HRMS analysis for the control plates were performed as previously described for the donor-drug plates.

In one embodiment, HPLC-HRMS analysis was performed on an Agilent 6545 LC/QTOF machine. The Autosampler compartment was kept at 7° C., and the column was kept at 25° C. Reverse phase chromatography was performed using an Agilent Eclipse Plus C18 RRHD column 1.8 µM (2.1×50 mm) column (Agilent, USA) with the gradient 95% A, 5% B to 5% A, 95% B in 12 minutes, then 95% B for 2 minutes, followed by initial conditions (95% A, 5% B) for 3 min to re-equilibrate the column (A=0.1% formic acid in water and B=0.1% formic acid in Acetonitrile). The flow rate was 0.4 ml/min. The samples in this study were run in one of two modes: a high resolution 4 GHz mode and a high dynamic range 2 GHz mode. MS acquisition parameters for the 4 GHz mode were set as follows: positive ion polarity, 0.5 min delay before MS measurement, 325° C. gas temperature, 10 L/min drying gas flow rate, 20 psi nebulizer pressure, 325° C. sheath gas temperature, 12

L/min sheath gas flow rate, 4000 V capillary voltage, 500 V nozzle voltage, 135 V fragmentor voltage, 45 V skimmer voltage, MS and MS/MS mass range of 100-1700 m/z, acquisition of 5 MS1 spectra/s, acquisition of 3 MS2 spectra/s, 20 eV collision energy, a maximum of 2 precursors per cycle, and a precursor selection threshold of 200 counts absolute or 0.01% relative. The system was run in auto MS/MS mode. For the 2 GHz mode, the parameters were the same as the 4 GHz mode with the following changes: acquisition of 8 MS1 spectra/s, acquisition of 6 MS2 spectra/s, maximum of 5 precursors per cycle, precursor selection threshold of 2000 counts.

To verify that the concentration of internal standard (voriconazole) used in the screen was below the saturation limit of the machine, a standard curve of voriconazole was constructed. 12 µL of 1 mM voriconazole was added to 228 µL of methanol and serial dilutions were performed by a factor of three to cover the concentration ranges of 40 µM to 0.165 µM. These samples were run on the 2 GHz setting described above to match the setting used for drug quantification in the screen.

Drugs and their detected metabolites were quantified in the MS1 of all samples using MassHunter Quantitative Analysis with the Agile2 integrator. The metabolites quantified here were either known metabolites (from prior screens or literature), or novel metabolites from the multi-donor screen identified using untargeted metabolomics and verified by molecular networking.

Following quantification, all further data processing was performed in MATLAB. For each plate, any samples whose internal standard AUC was greater than three interquartile ranges above the third quartile or below the first quartile was removed. In order to correct for differences in extraction efficiency, all peak areas in a given sample were divided by the corresponding internal standard area. This ratio was then used for hypothesis testing and all other downstream analyses. For drug depletion, unadjusted p-values were obtained by one-sided Welch's t-tests testing whether drug levels are significantly lower in the donor-drug conditions than in controls; p-values were computed for tests against controls where the drug was incubated with BG medium (medium-drug) and incubated with the heat-killed-microbiome (HKM-drug) controls. For metabolite production, unadjusted p-values were obtained for one-sided Welch's t-tests testing whether metabolite levels are significantly higher in donor-drug conditions than in control conditions; p-values were computed for tests against medium-drug, HKM-drug, as well as donor-DMSO (where the cultures are incubated with only the vehicle, DMSO) controls. Correction for multiple hypotheses was performed using the Benjamini-Hochberg procedure (Benjamini and Hochberg, 1995). Metabolite production and drug depletion p-values were adjusted separately. For depletion to be considered significant, FDR corrected p value<0.01 were required for both the medium-drug and HKM-drug adjusted p-values and also depletion was required to be greater than 50% relative to both controls. For metabolite production to be considered significant, FDR corrected p value<0.01 were required for the medium-drug, HKM-drug and donor-DMSO p-values.

Example Analysis Using an Untargeted Metabolomic Approach

In order to extract all features in a given sample, a batch recursive feature extraction method for small molecules and peptides within Profinder 8 (Agilent) can be used. The following settings in the method were changed from default: compound ion count threshold set to two ions, alignment retention time tolerance set to 0.2 min, minimum MFE score set to 90, minimum file prevalence set to 2, expected retention time set to ±1 min, retention time contribution to matching score set to 90, expected MS1 mass variation set to 10 ppm, expected retention time tolerance set to 0.2 min, absolute height threshold for EIC integration set to 2500 counts, and final absolute height threshold set to 5000. The resulting feature abundances were then analyzed in MAT-LAB. Any sample whose internal standard AUC is less than $10^6$ was removed. Hypothesis testing was then performed using similar statistical methods as for metabolite production in the targeted metabolomics, except that the multiple hypothesis correction of Storey (Storey, 2002) was used in place of the Benjamini-Hochberg method and require a fold-change cut-off of two relative to all controls. Features are combined if their retention times and estimated molecular weights differ by less than 0.2 min and 0.01 Da, respectively. All ions already quantified in the screen and all features that are statistically significant for more than one drug are removed.

For the remaining statistically significant features, molecular ion networking is used to verify the metabolite's relationship to the parent drug based on their HR-MS/MS fragmentation pattern. In order to gather data with a large enough number of MS2 spectra per parent ion samples of interest were rerun on the QTOF HPLC-HRMS/MS instrument (Agilent) using the same column and conditions, and the 4 GHz settings listed above (instead of the 2 GHz one used in the multi-donor screen). In order to minimize the number of samples run a second time, the minimal set of 81 samples was identified that would allow one to detect and perform molecular ion networking on all novel metabolites found in the original 1380 donor-drug samples. For molecular ion networking, the Global Natural Product Social Molecular Networking (GNPS) server was utilized, requiring that two ions have a cosine similarity of 0.5 and share at least 3 peaks in order to be linked. Connections were removed if the ions did not appear in each other's top 10 most similar ions. Molecular networks were visualized and mined using Cytoscape. In order to determine whether a metabolite is linked to its parent by the molecular ion networking, it is first identified whether the drug and metabolite are present in the network. For this, it was required that the mass and retention time found in the molecular ion networking differ by less than 0.2 min and 0.02 Da, respectively, from the properties reported by the initial donor-drug stage of the pipeline. The two compounds were considered related if they are in the same connected component of the graph. In the cases where either the metabolite or the parent drug or both were not picked up in the molecular ion networking analysis, the linkage was deemed "undetermined". There are several reasons why the metabolites or drugs are not picked up in the analysis, including the abundance of the ions and the number and abundance of fragment ions.

The MDMQ-Screen can be used in a variety of ways.

Figure 2:
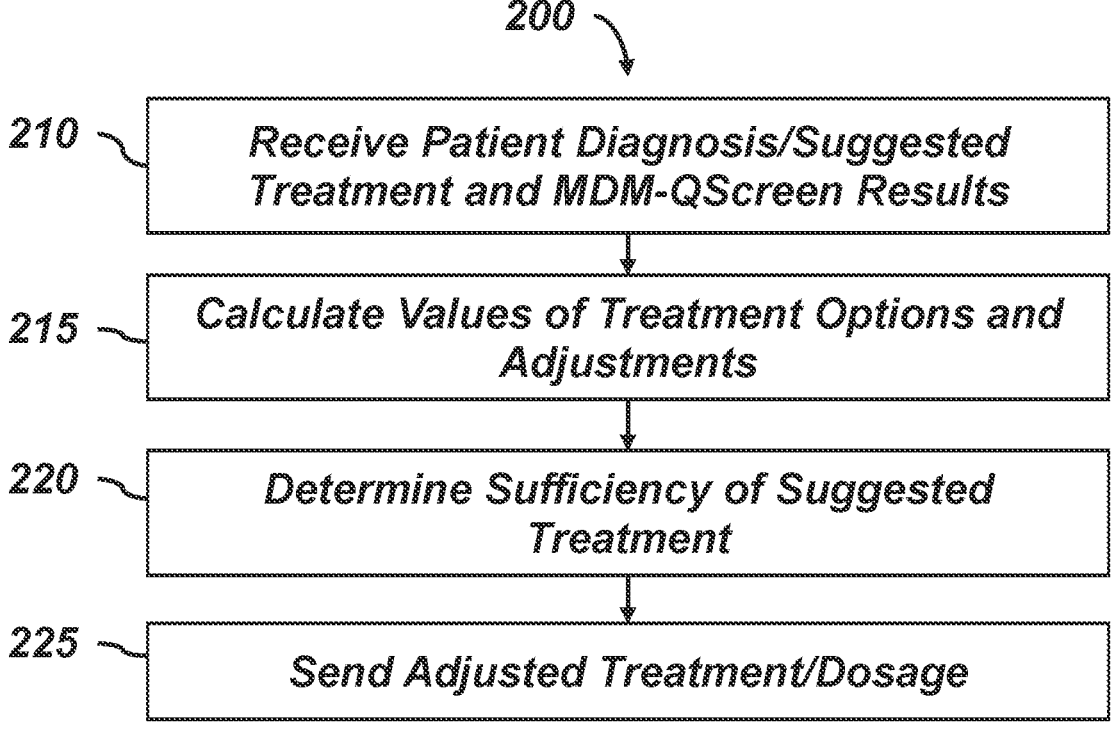
FIG. 2 is a flowchart for an embodiment of a disclosed system for providing alternative treatment or drug dosage regimes for a patient based on their microbiome.

For example, the MDMQ-Screen can be requested as part of a standard set of tests doctors may request to assess the health of a patient, as part of a personalized medicine approach. For example, with the MDMQ-Screen results, a doctor can choose a more optimal course of treatment specific to the patient. This approach could be automated. In one embodiment, illustrated in FIG. 2, a system is envisioned whereby non-transient computer readable media contains instructions that, when executed by one or more processors, causes the system to perform certain steps (200). The first step is to receive (210) a patient's MDMQ-Screen results and a diagnosis, a suggested treatment, or both.

Based on the MDMQ-Screen results, the one or more processors may then calculate (215) the relative values of the different available treatment options for that patient. For example, the one or more processors could provide weights for various factors, such as the difference in the drug's concentrations in the sample with the patient's microbiome vs. a control, the presence of a metabolite that is also effective in treating the condition, the presence of a toxic metabolite in the microbiome sample that is not present in a control sample, and differences between a microbiome sample with the suggested treatment and a microbiome sample with an alternate treatment. By summing the weighted factors, the one or more processors can identify a best option (e.g., the option with the greatest sum of weighted factors). In some embodiments, other data, such as drug costs, severity of side effects, patient age, weight, etc., are considered when determining the values of the treatment options. This step may also include calculating how much of an adjusted dosage is required, based on the difference in the drug's concentrations in the sample with the patient's microbiome vs. a control. For example, for a suggested treatment that calls for 10 mg of an active material, if the MDMQ-Screen reveals the patient's biome eliminates 50% of the active material vs. a control, the one or more processors can calculate that a 20 mg dosage may be required, and the relative weights of that altered dosage can be taken into account in this step. The one or more processors will need to be operatively connected to a database containing alternative treatment options for various conditions. For example, the database may contain information such as a condition, an active material for treating that condition, and a dosage required to treat that condition as appropriate for whatever condition is being treated (e.g., amount per unit weight of the patient, standard dosages, etc.). The one or more processors can use information from the database to inform their calculations regarding the weights of the various treatment options.

Once the values are calculated, the system can determine (220) whether the suggested treatment is sufficiently optimal. In some embodiments, the one or more processors could determine if a doctor's suggested treatment or dosage is the optimal approach. In some embodiments, the one or more processors could determine if the difference between the sum of the weighted factors for the doctor's suggested sub-optimal approach and the sum of weighted factors for the optimal approach is greater than a particular threshold. That is, because it is known that several acceptable "good" options for treating a condition may exist, the system might only suggest a different approach if the doctor's approach is clearly not one of those "good" options, even if the doctor's approach is not actually the most optimal approach determined by the system.

In some embodiments, where the MDMQ-Screen determines the interference of the microbiome is less or absent in a different approach than the one suggested by the doctor, a different treatment (e.g., different active material and/or different drug) may be suggested. That is, in some cases, the results of the MDMQ-Screen may indicate that either the dosage needs to change, or that the particular drug is not suitable for the patient and that the drug needs to change.

If the doctor's proposed treatment is not sufficiently optimal, the one or more processors would then send (225) at least the optimal adjusted treatment and/or dosage option to a display, a database, or some other device to communicate the suggestion to an appropriate individual (such as a doctor, the patient, etc.). In some cases, multiple options may be sent, or all options may be sent, with an indication of the relative rank of the option. The doctor or other individual could then decide whether to act on that information—for example, whether to adjust the treatment or dosage as suggested.

Figure 3:
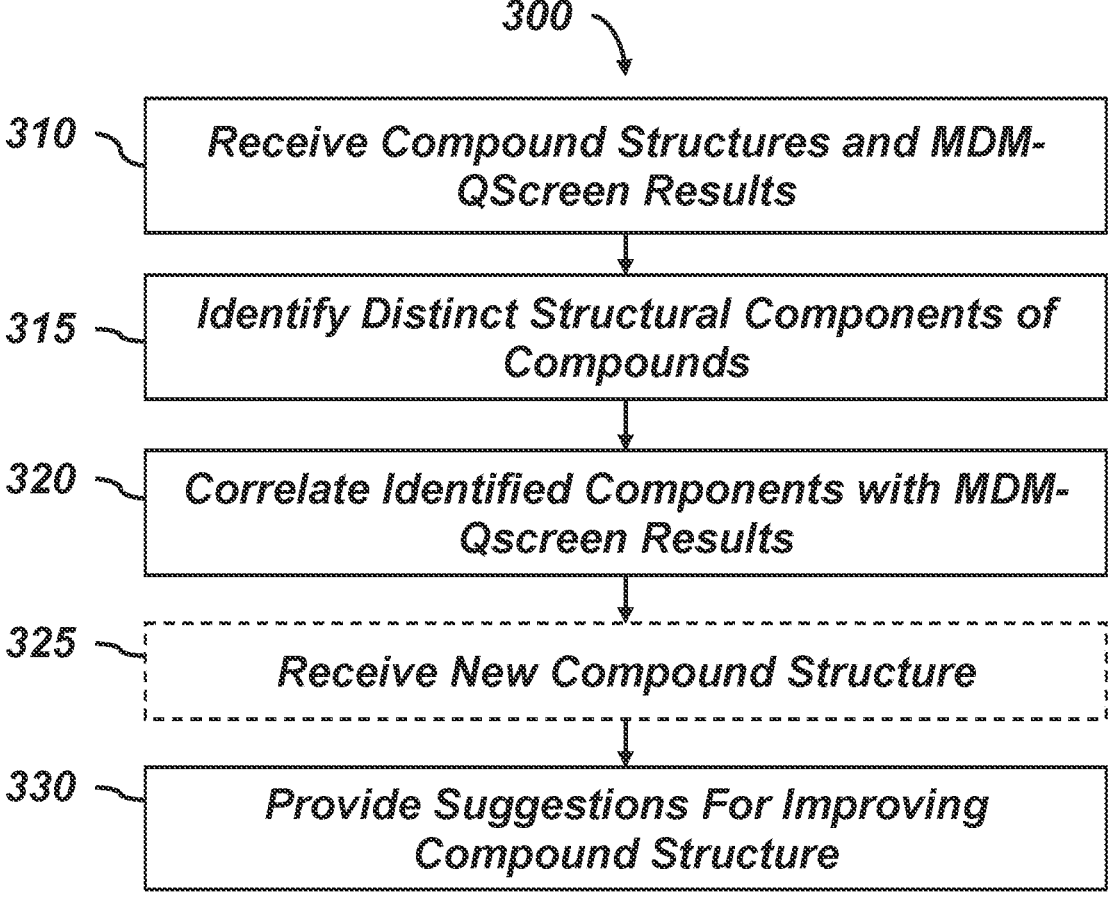
FIG. 3 is a flowchart for an embodiment of a disclosed system for assisting drug development using microbiomes.

Alternatively, the MDMQ-Screen could be utilized during drug development. For example, a given panel of microbiome sample donors, many possible drugs can be screened during the drug discovery phase, for use in guiding drug development. For example, the results from the MDMQ-Screen could be utilized to determine if there are certain functional groups that cause undesirable metabolites to form. As seen in FIG. 3, in one embodiment, a system is envisioned whereby non-transient computer readable media contains instructions that, when executed by one or more processors, causes the system to perform certain steps (300). The first step is to receive (310) MDMQ-Screen results from a plurality of individuals, preferably, a fixed panel of individuals, and the structures of compounds that were used in the MDMQ-Screen as actives. The one or more processors would then identify (315) distinct structural components of the received compounds. Each component may by one or more atoms in a compound. Each component may include one or more functional groups and/or parts of functional groups. In some embodiments, a trained machine learning algorithm is provided to extract the necessary features and identify the structural components. These components would then be correlated (320) with MDMQ-Screen results. For example, once a plurality of compounds are tested, the relative impact of each component on MDMQ-Screen results could then be assessed and given a score. This could be accomplished via various statistical approaches. The system may then optionally receive (325) a new compound structure for consideration. The system could then provide suggestions (330) for improving the new structure, or one or more of the previously received compound structures, based on the correlations. For example, the one or more processors may suggest replacements for existing components on a given structure or suggest components that should be removed entirely from the structure.

Alternatively, the MDMQ-Screen could be utilized in clinical trials. In some embodiments, after receiving MDMQ-Screen results, a person could be eliminated or added to a clinical trial. For example, if it is recognized that a given person's microbiome converts a significant portion of the active material, that person might not be an appropriate subject for the clinical trial. In another example, the results of MDMQ-Screen could be incorporated in the clinical trial analyses as an additional parameter, ensuring a more informed clinical trial.

Example of Multiple Subject Analysis

To accommodate multiple subjects, a generalizable quantitative metric for assessing the best culturing medium for microbiome samples was needed. In the analysis of a single subject's ex vivo cultures, a variety of metrics were applied, and found a medium that was the best trade-off between richness, evenness, and compositional similarity. However, this approach is not scalable to a large number of donors and also ignores the role of community biomass, which may lead to suboptimal media selection. A metric called Expected Number of Detectable Strains (ENDS) was developed, a corrected richness metric where the contribution of each ASV is weighed by the probability that its metabolite can be detected while considering total biomass ENDS utilizes two data inputs related to the ex vivo culture composition: relative abundance at a given taxonomic level and total community biomass, and two inputs related to the instrument detection sensitivity: a model of instrument background noise and a model of instrument measurement noise. Using this information, a simple mechanistic model of MDM metabolite production, and estimations of statistical power, the probabilities that metabolic reactions performed by each strain will be detected in the ex vivo culture can be computed.

Figure 4A:
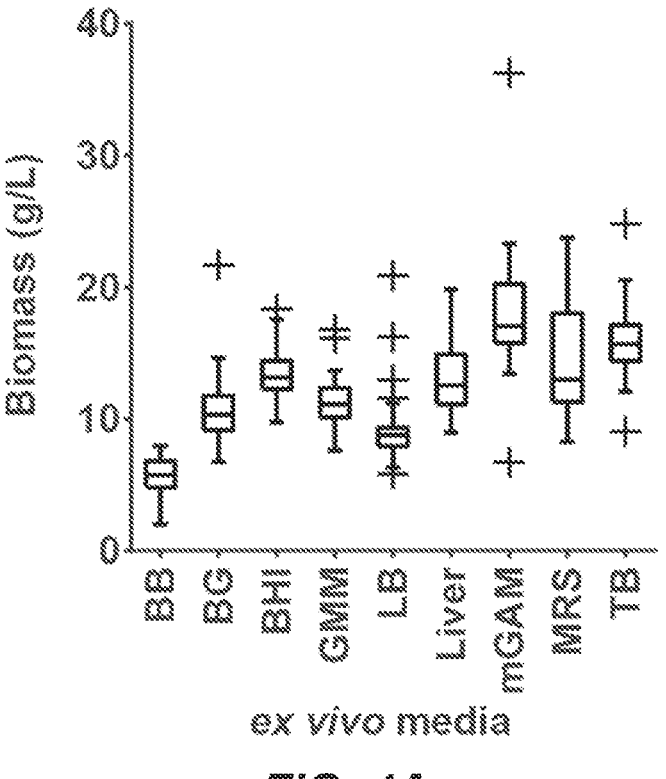
FIG. 4A is a Histogram of ex vivo community biomass for all donors in different media conditions.

With this quantitative framework in hand, fresh fecal samples were collected from 20 healthy donors (D1-20). Each sample was cultured in nine representative media and used 16S rDNA sequencing to determine the composition of the cultured communities as previously described. To measure community biomass, 30 μl from each donor glycerol stock was cultured in 10 different pre-reduced media. One ml was harvested from each culture after 48 hours and centrifuged to recover the resulting bacterial pellets. The pellets were weighed in Eppendorf tubes and the mass was subtracted from that of the empty tube prior to pellet collection. A wide variation in culture characteristics was observed, with the richness ranging from 20-135 ASVs and biomass density ranging from 2-27.9 g/L. See FIG. 4A. mGAM and BB media consistently performed well with all 20 donors. Interestingly, mGAM had moderate ASV richness and high biomass, while BB yielded a much lower biomass with high richness and did not suffer from the Enterobacteriaceae expansion observed in mGAM. It was calculated that a 70/30 BB/mGAM mixture would yield an optimal medium with moderate biomass, high richness, and a reduced Enterobacteriaceae expansion, thus this mixture (named BG) was included as a $10^{th}$ medium in the culturing trials.

Figure 4B:
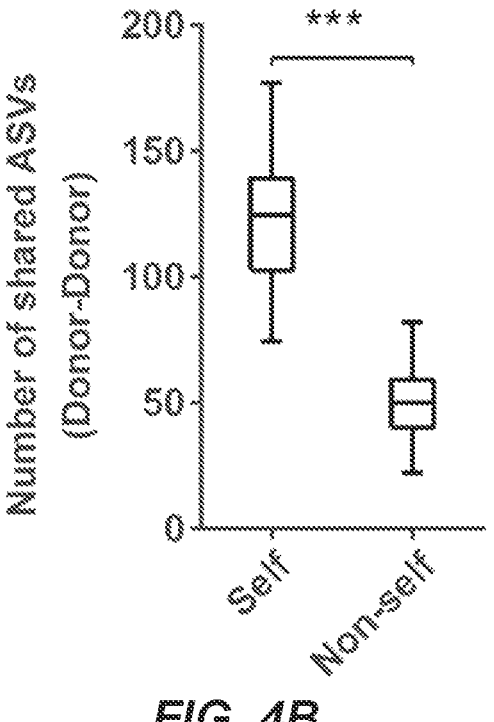
FIG. 4B is a graph comparing shared ASVs within (self, i.e., the ASV richness) and between (non-self) donor fecal samples. '***' indicates p<0.001, permutation test.
Figure 4C:
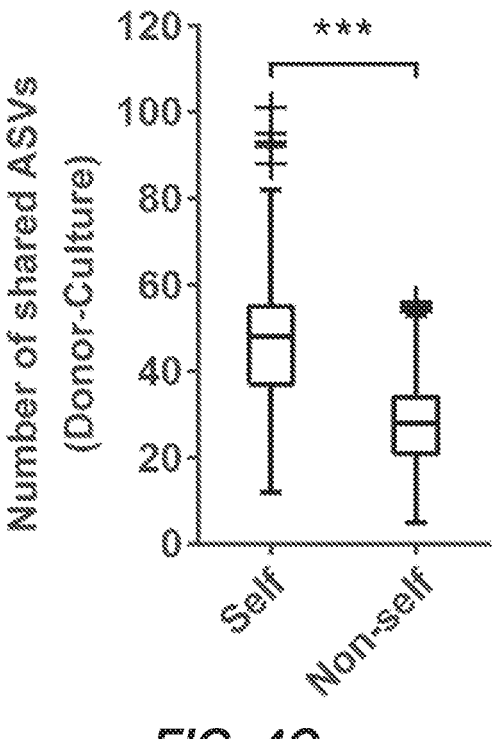
FIG. 4C is a graph comparing shared ASVs between donor fecal samples and ex vivo cultures originating from the same donor (self) versus ones originating from other donors (non-self). '***' indicates p<0.001, permutation test.

Next, it was wondered whether the ex vivo cultured communities are truly personalized per subject, an important prerequisite if cultured communities are to be used for assessing inter-individual variability in MDM. Personalization between cultures was clearly observed at the ASV level, with clear specific patterns unique to individual donors and their cultures. Significantly more ASVs were found to be shared between donor feces and their self ex vivo cultures than non-self (47.1 vs. 27.5 ASVs, p<0.001, permutation test), partially recapitulating the inherent personalization between the donor fecal samples. See FIGS. 4B, 4C. Moreover, 167 ASVs were identified that were unique to one of the 20 donors in their fecal samples (8.4 ASVs per donor on average) and were concordantly unique to the same donor in their ex vivo cultures. Finally, multiple replicates of mGAM and BG ex vivo cultures were grown and sequenced from different donors (all 20 donors, three replicates each for BG, and eight donors, six replicates each for mGAM). The analysis of these replicates, whether cultured from the same or separate glycerol stock aliquots, revealed a high correlation between ASV abundances of replicates from the same donor and ensured that the community assembly process was replicable (Pearson correlation coefficient >0.9). These analyses confirm that the approach results in personalized and replicable microbial communities.

Figure 4D:
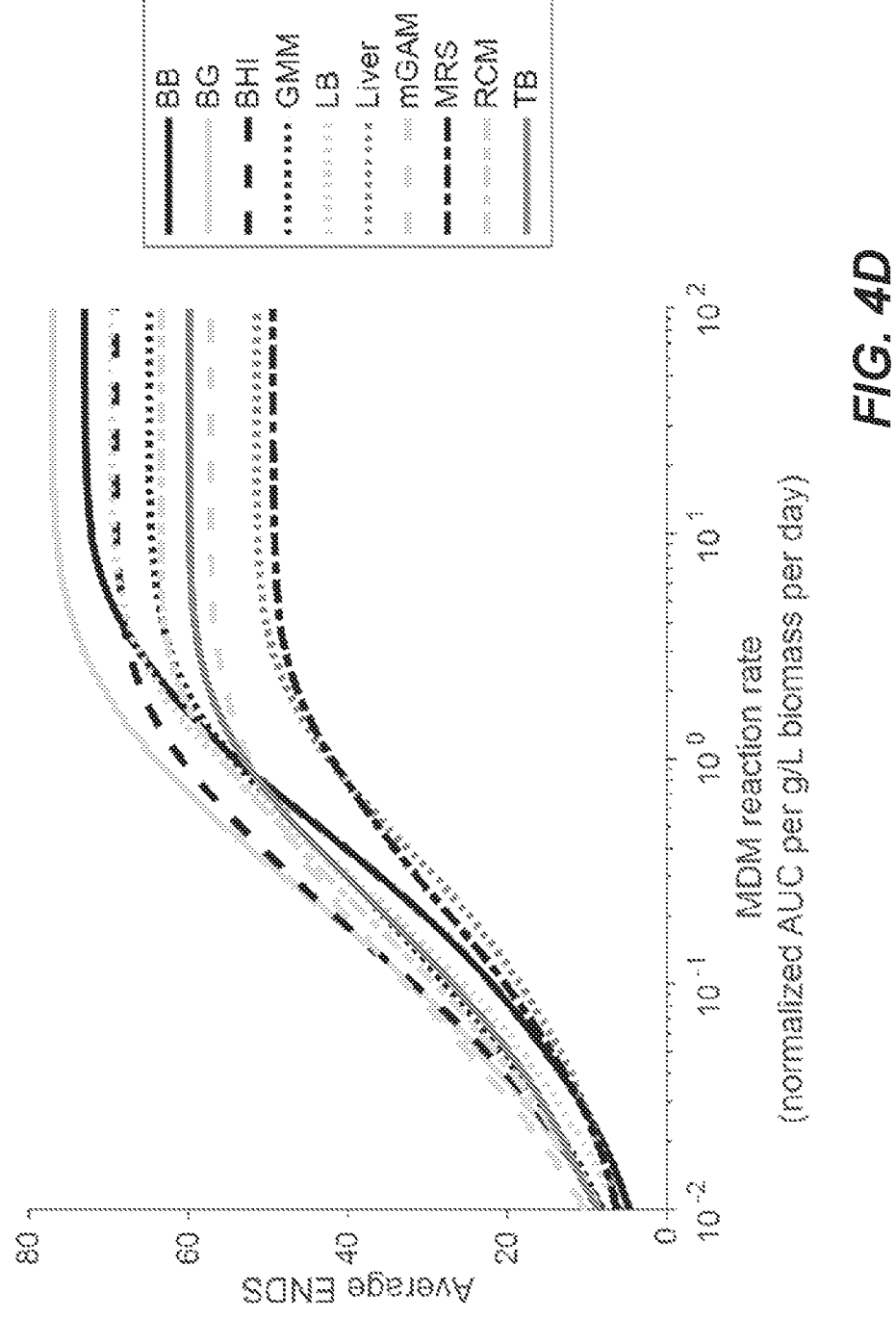
FIG. 4D is a graph of the average ENDS of different media conditions at varying metabolite production rates (quantified as AUC normalized to an internal standard). ENDS was computed for each ex vivo culture assuming a p-value significance cutoff of 0.01 and three replicates. For each media condition, ENDS was averaged across all donors.
Figure 4E:
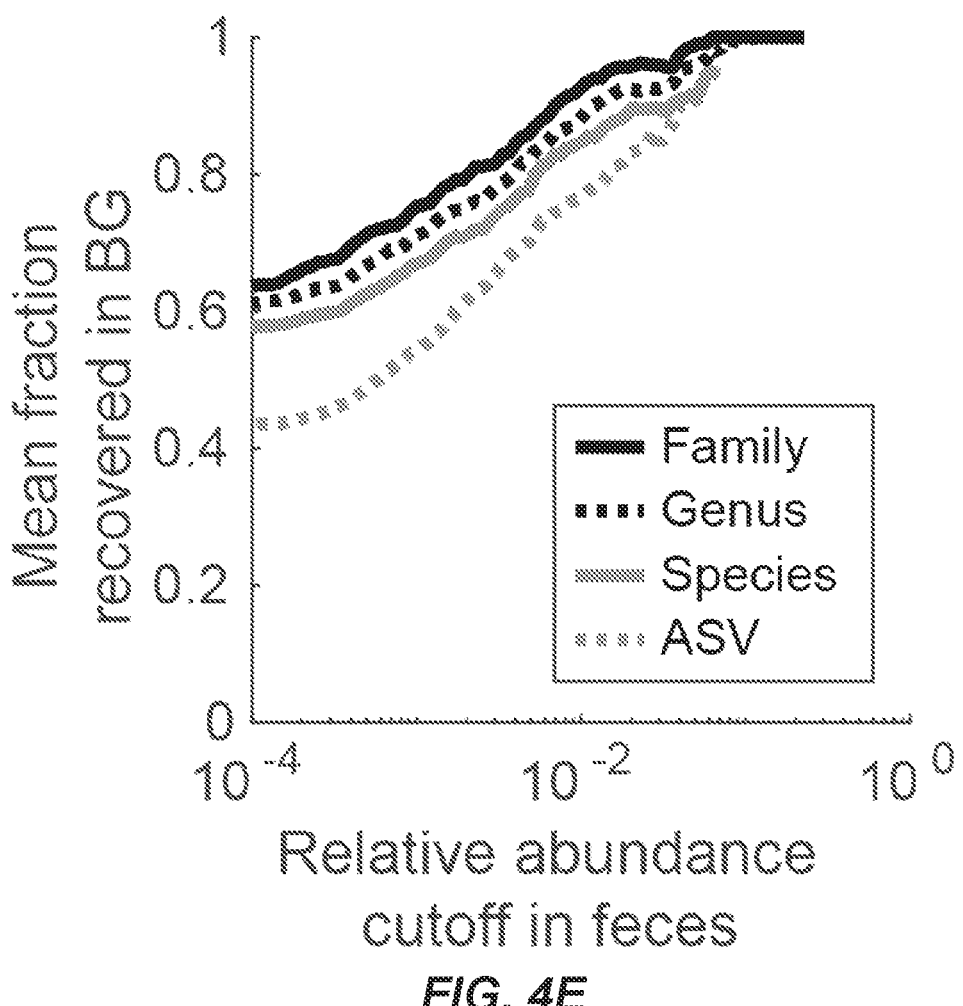
FIG. 4E is a graph of the average fractional recovery of different taxa in BG ex vivo communities as a function of relative abundance in the original donor fecal sample. The fractional recovery was calculated for all donors and then averaged.

To select a single medium that would be on average optimal for use in a 20-donor screen, the average ENDS of all media across a range of reaction rates (e.g., between $10^{-2}$ and $10^2$ normalized area under the curve per g/L biomass per day) was computed. See FIG. 4D. It was found that BG is on average an optimal medium at reaction rates estimated to be the most physiologically relevant. In addition, BG recapitulates a large portion of the microbial community in the original fecal sample. On average, BG cultures recover 76.6% of the ASVs above 1% in the original fecal sample, which translates to 84.7%, 88.3%, 92.7% recovery rate on the species, genus, and family levels of taxa above 1% in the original sample, respectively. See FIG. 4E. In terms of recovery of all elements, BG recovers 43.3%, 57.3%, 60.6%, and 62.8% on the ASV, species, genus, and family levels, respectively. BG is also on average the closest in composition to the original sample ($D_{JS}$=0.16) and has the highest average diversity (H=4.3). BG was therefore selected as the medium to use in this 20-donor screen.

A high throughput quantitative metabolomic approach was developed to assess MDM inter-individual variability with a subset of drugs. All experimental steps including incubation, chemical extraction, and HPLC-HRMS analysis were performed in microtiter 96-well plates instead of individual tubes, at a 400 µl volume instead of 3 ml. This lowered the amount of drug used per incubation, allowing the performance of triplicated reactions simultaneously, and streamlined the chemical extraction and analysis procedures. The approach also includes spiking a known concentration of an internal standard prior to the chemical extraction, which allows one to precisely quantify partial, in addition to complete, drug depletion.

A 23-drug subset was chosen to test the ability of the quantitative approach to reveal potential inter-individual variabilities in MDM under the MDMQ-Screen conditions. Thirteen drugs had at least one defined metabolite with a known chemical structure, which allowed an unambiguous comparison of their levels between samples. For all 20 donors, ex vivo cultures (in BG medium) were incubated in triplicates in a 96-well microtiter plate with each of the 23 drugs at a final concentration of 33 µM, or with DMSO. In addition, an abiotic medium-drug plate as well as a heat-killed-microbiome-drug (HKM-drug) plate were prepared in the same manner. After 24-hour incubation, culture and control plates were chemically extracted and analyzed using HPLC-HRMS.

Figure 4F:
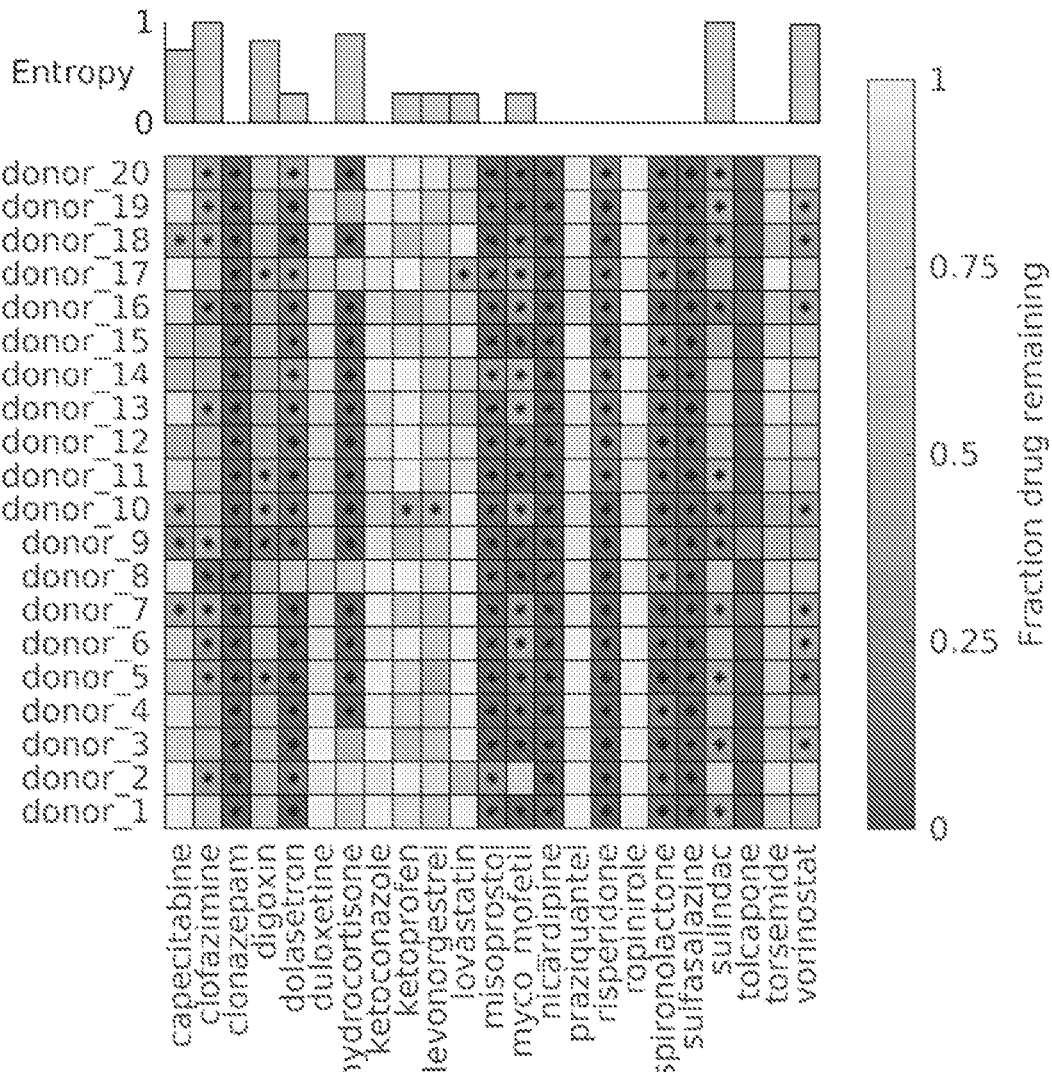
FIG. 4F is a heat map of drug depletion showing the mean fraction of drug remaining after 24 hours for each donor-drug combination. The fraction remaining is computed relative to the medium-drug control, and fractions above 1 are truncated to 1 for simplicity.

The percent drug remaining and metabolite level was calculated, to assess drug depletion and metabolite production in the presence of microbiome cultures, respectively. Both metrics were calculated using Area Under the Curve (AUC) integration with normalization to the internal standard. Statistical significance was determined for metabolite production using a one-sided Welch's t-tests between the donor-drug condition and the donor-DMSO, medium-drug, and HKM-drug conditions and corrected the resulting p-values for multiple hypotheses using the Benjamini-Hochberg method, requiring that tests against all three control conditions be significant at a level of 0.01. For drug depletion, the same method was used with the donor-drug and HKM-drug conditions as controls and included an additional fold-change cutoff of two. See FIG. 4F.

Untargeted metabolomics analyses were performed for new metabolite discovery, by identifying unique molecular features from all samples, determining statistical significance using similar methods as for the targeted metabolomics, and verifying the metabolite's relationship to the parent drug based on their HRMS/MS fragmentation pattern.

Specifically, in order to extract all features in a given sample, the batch recursive feature extraction method for small molecules and peptides within Profinder 8 (Agilent) was used. The following settings in the method were changed from default: compound ion count threshold set to two ions, alignment retention time tolerance set to 0.2 min, minimum MFE score set to 90, minimum file prevalence set to 2, expected retention time set to 1 min, retention time contribution to matching score set to 90, expected MS1 mass variation set to 10 ppm, expected retention time tolerance set to 0.2 min, absolute height threshold for EIC integration set to 2500 counts, and final absolute height threshold set to 5000. The resulting feature abundances were analyzed in MATLAB. Any sample whose internal standard AUC is less than $10^6$ was removed. Hypothesis testing was performed using similar statistical methods as for metabolite production in the targeted metabolomics, except that the multiple hypothesis correction of Storey was utilized in place of the Benjamini-Hochberg method and a fold-change cut-off of two relative to all controls was required. Features were combined if their retention times and estimated molecular weights differ by less than 0.2 min and 0.01 Da, respectively. All ions already quantified in the screen and all features that are statistically significant for more than one drug were also removed.

For the remaining statistically significant features, molecular ion networking was used to verify the metabolite's relationship to the parent drug based on their HR-MS/MS fragmentation pattern. In order to gather data with a large enough number of MS2 spectra per parent ion samples of interest were rerun on a QTOF HPLC-HRMS/MS instrument (Agilent) using the same column and conditions, and 4 GHz settings (positive ion polarity, 0.5 min delay before MS measurement, 325° C. gas temperature, 10 L/min drying gas flow rate, 20 psi nebulizer pressure, 325° C. sheath gas temperature, 12 L/min sheath gas flow rate, 4000 V capillary voltage, 500 V nozzle voltage, 135 V fragmentor voltage, 45 V skimmer voltage, MS and MS/MS mass range of 100-1700 m/z, acquisition of 5 MS1 spectra/s, acquisition of 3 MS2 spectra/s, 20 eV collision energy, a maximum of 2 precursors per cycle, and a precursor selection threshold of 200 counts absolute or 0.01% relative).

Figure 4G:
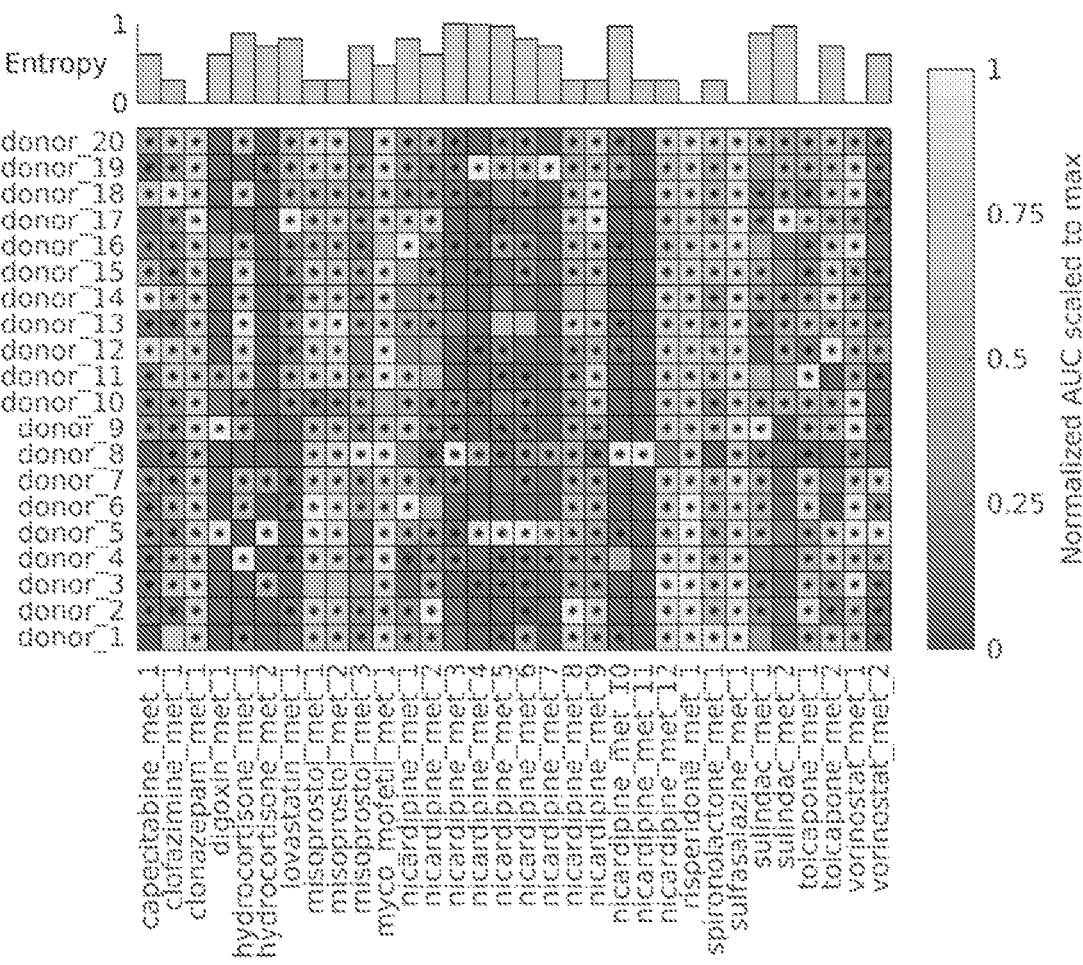
FIG. 4G is a heat map of metabolite production showing the mean level of metabolite after 24 hours, normalized to the maximum level of that metabolite across all donors. Metabolites with a star next to their name were discovered using the untargeted metabolomics approach, while those without stars were discovered previously.

In order to minimize the number of samples run a second time, the minimal set of 81 samples that would allow us to detect and perform molecular ion networking on all novel metabolites found in the original 1380 donor-drug samples was identified. For molecular ion networking, the Global Natural Product Social Molecular Networking (GNPS) server was used, with the same settings from the single-donor example. In order to determine whether a metabolite is linked to its parent by the molecular ion networking, it was first identified whether the drug and metabolite are present in the network. For this, it was required that the mass and retention time found in the molecular ion networking differ by less than 0.2 min and 0.02 Da, respectively, from the properties reported by the initial donor-drug stage of the pipeline. The two compounds was called related if they are in the same connected component of the graph. In the cases where either the metabolite or the parent drug or both were not picked up in the molecular ion networking analysis, the linkage was deemed "undetermined". There are several reasons why the metabolites or drugs are not picked up in the analysis, including the abundance of the ions and the number and abundance of fragment ions. All verified metabolites from the untargeted metabolomics approach were then quantified using the same targeted metabolomics workflow described above. See FIG. 4G.

Cases of consistently negative MDM across donors (keto-conazole, praziquantel, ropinirole, and torsemide), consistently positive MDM in either drug depletion (misoprostol, nicardipine, spironolactone), metabolite production (tolca-pone, vorinostat), or both (clonazepam, risperidone, and sulfasalazine), and variable MDM were observed. This variability was in drug depletion (ketoprofen, levonorg-estrel), metabolite production (misoprostol, nicardipine, spironolactone), or both (capecitabine, clofazimine, digoxin, hydrocortisone, lovastatin, mycophenolate mofetil, sulin-dac, vorinostat). This variability was quantified by computing the Shannon entropy (in base 2) of the distribution of metabolizers and non-metabolizers, denoted as $H_V$. This metric is maximal ($H_V$=1) when half of donors metabolize the drug and is minimal when the drug is either always or never metabolized ($H_V$=0).

Figure 4H:
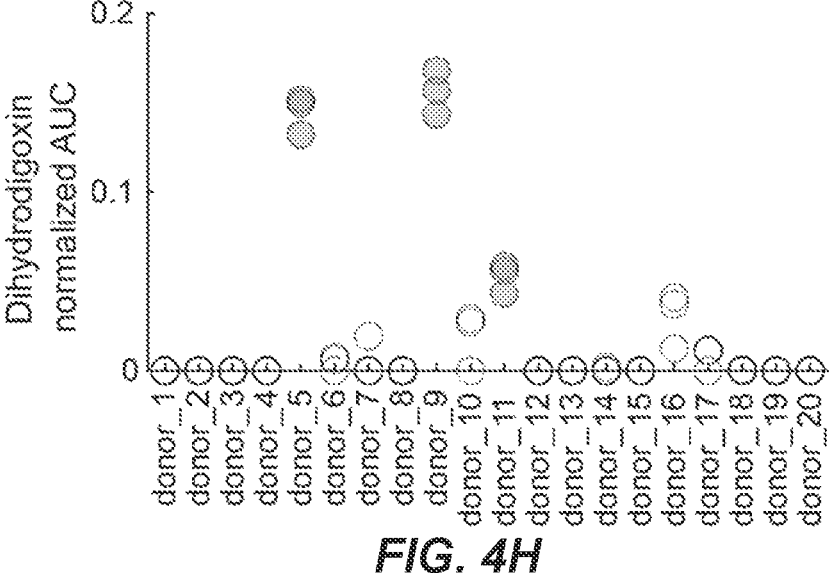
FIG. 4H is a graph of levels of metabolite production (measured by HPLC-HRMS in AUC normalized to an internal standard) for dihydrodigoxin, with the variability entropy indicated above. Filled data points indicate that the replicates are significantly higher than control conditions.

The observed variability ranged widely from 1/20 to 19/20 donors deemed MDM+ for a given type of drug depletion or metabolite production. In the case of digoxin, for example, 3/20 donors ($H_V$=0.61) produced the known metabolite dihydrodigoxin in statistically significant amounts (see FIGS. 4F, 4H). Inter-individual variability in digoxin MDM has been clinically known for decades, where significant reduction of the drug into dihydrodigoxin and related metabolites occurs in only a subset of patients. These results demonstrate that this screen can quantitatively assess the inter-individual variability of MDM between personalized gut microbial communities cultured under identical ex vivo conditions.

Figure 4I:
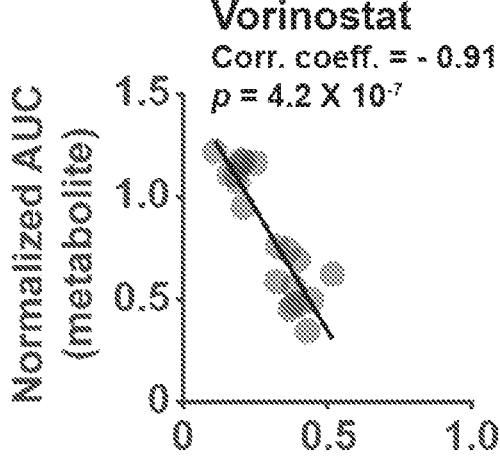
FIG. 4I is a graph showing a (significantly negative) correlation between drug depletion and metabolite production, for digoxin, with the Pearson correlation coefficient indicated above. The line shown is a linear regression fit of the data.
Figure 4J:
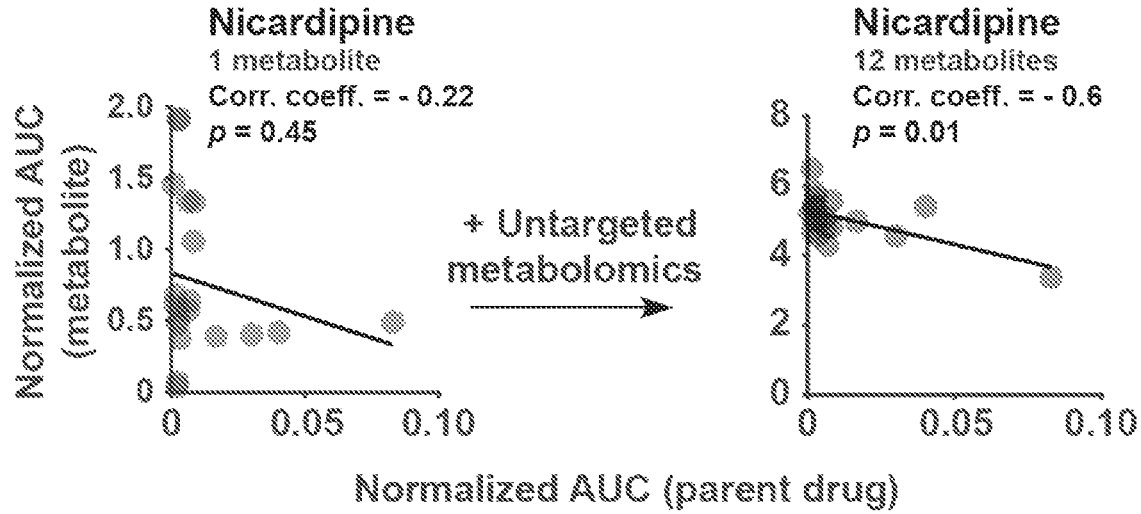
FIG. 4J is a graph showing the correlation between drug depletion and metabolite production for nicardipine before and after inclusion of metabolites discovered by untargeted metabolomics.

Next, it was sought to determine whether the depletion of drugs in the screen can be explained by the production of associated metabolites. If changes in drug levels are primarily due to conversion to a detected metabolite, there should exist a strong negative correlation between depletion and metabolite production, corresponding to a stoichiometric mass balance. The absence of such a correlation, on the other hand, would suggest additional events that are not accounted for (e.g., the production of additional unknown or undetectable metabolites, the conversion of the initial metabolite into a third one, or bacterial consumption of the parent drug). For drugs with variable MDM ($H_V$>0.5 for at least one metabolite or the parent drug), the Pearson correlation coefficient of the drug signal and the sum of known metabolite signals was computed in all donor-drug ex vivo samples. It was then determined whether a drug has statistically significant correlation by performing t-tests, correcting p-values using the Benjamini-Hochberg method, and requiring FDR corrected p<0.01. For vorinostat, for example, significant negative correlation was found between metabolite production and drug depletion (Pearson correlation coefficient of –0.91), suggesting that the majority of drug depletion can be explained by the production of the quantified metabolite. See FIG. 4I. Nicardipine, on the other hand, exhibited a very poor correlation initially (Pearson correlation coefficient of –0.22), implying that additional unknown factors are at play. Interestingly, the untargeted metabolomics pipeline detected 11 additional metabolites of nicardipine, which upon inclusion in the analysis resulted in a stronger negative correlation (Pearson correlation coefficient of –0.6, FDR corrected p=0.0102). See FIG. 4J. Since the screen is based on microbial communities and not individual strains, it provides a powerful platform to discover interacting factors that influence drug and metabolite levels under realistic conditions—as exemplified by the varying number of nicardipine metabolites observed per personalized community.

Next, it was assessed whether one could predict MDM using taxonomic data. Spearman correlations were calculated between absolute abundances of taxonomic elements (at different levels) in the BG ex vivo cultures and measured drug and metabolite levels in matching donors but found no significant correlations—even in specific cases of MDM where metabolism has been previously attributed to a single species (e.g., digoxin reduction by *Eggerthella lenta*). Specifically, the drugs and metabolites tested were restricted by requiring that they must have at least one associated compound (parent drug or metabolite) with an inter-individual variability entropy >0.5, and that there exists at least one sample with more than 20% of the drug remaining relative to medium-drug controls. Only taxonomic elements present in at least three samples with a biomass of at least 1 mg/L in at least one sample were tested, and the resulting p-values were corrected for multiple hypotheses at each taxonomic level using the Benjamini-Hochberg method. The n for these tests is based on the number of observations used to compute the correlations. Spearman correlation was computed for this analysis. The mean BG community composition for each donor was used for the correlation analysis. Taxonomic elements at the ASV, species, genus, and family levels were tested.

This lack of significant correlation is likely due to a combination of two factors. First, as has been previously observed, taxonomic classifications may not reflect the presence or absence of gene variants that encode strain-specific drug-metabolizing enzymes, even at the ASV level. Second, the observed level of MDM may not be monotonically dependent on a single taxon's abundance if confounding community effects are at play. Examples of such effects include the contribution of several community members to the production of the metabolite(s), the consumption of the drug or metabolite(s), or the inhibition of the metabolite producing or drug depleting bacterium or enzyme. These results emphasize the importance of considering whole community effects in MDM. While the ex vivo communities may not fully recapitulate all possible community effects that occur in humans, they represent an important step towards identifying and quantifying them.

Those skilled in the art will recognize or be able to ascertain using no more than routine experimentation, many equivalents to the specific embodiments of the invention described herein. Such equivalents are intended to be encompassed by the following claims.

What is claimed:

1. A method for quantitatively assessing drug metabolism, comprising:
   a. providing at least one fecal sample from at least one donor;
   b. preserving at least a portion of the at least one fecal sample;
   c. producing an ex vivo culture of a donor microbiome from the at least one fecal sample in a predetermined medium, wherein the predetermined medium is selected utilizing a metric in which the contribution of each amplicon sequence variant (ASV) is weighed by the probability that its metabolite can be detected while considering total biomass;
   d. incubating the ex vivo culture of the donor microbiome with at least one active material;
   e. chemically extracting a sample from the ex vivo culture and a control sample;
   f. analyzing the extracted samples, quantifying active material and metabolite levels in at least one of the extracted samples using a quantitative targeted metabolomics assessment.

2. The method according to claim 1, further comprising identifying a novel metabolite in the extracted sample from the ex vivo culture using a quantitative untargeted metabolomics assessment.

3. The method according to claim 1, wherein the control sample and the sample from the ex vivo culture both comprise a metabolite, and wherein quantifying active material and metabolite levels comprises determining whether the sample from the ex vivo culture contains a different metabolite, or a different level of the same metabolite as compared to the control sample.

4. The method according to claim 3, wherein the different metabolite is a derivative of the at least one active material.

5. The method according to claim 1, wherein quantifying active material and metabolite levels comprises determining whether the at least one active material can be detected in the control sample and not detected in the sample from the ex vivo culture.

6. The method according to claim 1, wherein the at least one active material comprises a pharmaceutical composition intended to be taken orally.

7. The method according to claim 1, wherein the at least one active material comprises a pharmaceutical composition intended to be taken non-orally.

8. The method according to claim 1, wherein the at least one active material is present in the incubated ex vivo culture at a concentration ≤50 μM.

9. The method according to claim 1, wherein the donor microbiome is a human gut microbiome.

10. The method according to claim 1, wherein at least a portion of each fecal sample is preserved by bringing each fecal sample into an anaerobic environment, suspending a portion of each fecal sample in a sterile buffer with an amino acid, allowing a supernatant to form, and mixing the supernatant with a preservative at a predetermined ratio.

11. The method according to claim 10, wherein the sterile buffer is sterile phosphate buffer supplemented with L-cysteine, wherein the L-cysteine is present in the sterile phosphate buffer in an amount less than 0.5 wt %.

12. The method according to claim 10, further comprising freezing the mixture after the preservative has been added.

13. The method according to claim 1, wherein the predetermined medium is selected from the medium having the highest value for Expected Number of Detectable Strains (ENDS).

14. The method according to claim 1, wherein the extracted samples are analyzed using High Performance Liquid Chromatography coupled with High-Resolution Mass Spectrometry (HPLC-HRMS).

\* \* \* \* \*